United States Patent
Yamaguchi et al.

(10) Patent No.: US 9,555,431 B2
(45) Date of Patent: Jan. 31, 2017

(54) DISCHARGE SYSTEM AND METHOD OF DISCHARGE BY A DISCHARGE SYSTEM

(71) Applicant: MICROJET CORPORATION, Shiojiri-shi (JP)

(72) Inventors: Shuichi Yamaguchi, Shiojiri (JP); Hisashi Takeuchi, Shiojiri (JP); Tomoya Kurashina, Shiojiri (JP)

(73) Assignee: MICROJET CORPORATION, Shiojiri-Shi, Nagano (JP)

( * ) Notice: Subject to any disclaimer, the term of this patent is extended or adjusted under 35 U.S.C. 154(b) by 28 days.

(21) Appl. No.: 14/396,677

(22) PCT Filed: Apr. 24, 2013

(86) PCT No.: PCT/JP2013/002798
§ 371 (c)(1),
(2) Date: Oct. 23, 2014

(87) PCT Pub. No.: WO2013/161300
PCT Pub. Date: Oct. 31, 2013

(65) Prior Publication Data
US 2015/0090807 A1    Apr. 2, 2015

(30) Foreign Application Priority Data

Apr. 24, 2012    (JP) ................ 2012-099059

(51) Int. Cl.
*B05C 11/10* (2006.01)
*B05B 12/08* (2006.01)
(Continued)

(52) U.S. Cl.
CPC ............. *B05B 12/08* (2013.01); *B01L 3/0268* (2013.01); *B05B 12/06* (2013.01); *B05B 12/082* (2013.01);
(Continued)

(58) Field of Classification Search
USPC ....... 118/300, 313–315, 712, 666, 665, 694; 422/501, 509, 518, 552
See application file for complete search history.

(56) References Cited

U.S. PATENT DOCUMENTS 4,844,298 A * 7/1989 Ohoka ................ B01L 3/0279
141/104
5,045,286 A * 9/1991 Kitajima ............. B01L 3/0275
141/130

(Continued)

FOREIGN PATENT DOCUMENTS

JP    7-333231 A    12/1995
JP    10-038898 A    2/1998

(Continued)

OTHER PUBLICATIONS

Notification of Transmittal of Translation of the International Preliminary Report on Patentability (Forms PCT/IB/338 and PCT/IB/373) and the Written Opinion of the International Searching Authority (Form PCT/ISA/237) issued on Nov. 6, 2014, by the International Bureau of WIPO in corresponding International Application No. PCT/JP2013/002798. (8 pages).

(Continued)

*Primary Examiner* — Yewebdar Tadesse
(74) *Attorney, Agent, or Firm* — Buchanan Ingersoll & Rooney PC (57) ABSTRACT

A discharge system includes: a head unit including discharge heads that discharge a liquid material from nozzle openings that are communication with cavities onto a target by changing the internal pressure of the cavities using piezo elements; a viscosity estimating unit that estimates the viscosity of the liquid material by sucking the liquid material from first vessels that hold the liquid material into the cavities; and a waveform control unit that controls the (Continued)

voltage applied to the piezo elements according to the estimated viscosity of the liquid material.

14 Claims, 9 Drawing Sheets

(51) Int. Cl.
*B01L 3/02* (2006.01)
*B05B 12/06* (2006.01)
*B05B 12/10* (2006.01)
*B05B 17/00* (2006.01)
*G01N 11/06* (2006.01)
*G01N 35/10* (2006.01)

(52) U.S. Cl.
CPC ............... *B05B 12/10* (2013.01); *B05B 17/00* (2013.01); *B05C 11/101* (2013.01); *B05C 11/1005* (2013.01); *B01L 2200/146* (2013.01); *B01L 2400/0439* (2013.01); *G01N 11/06* (2013.01); *G01N 2035/1041* (2013.01)

(56) References Cited

U.S. PATENT DOCUMENTS

| | | | |
|---|---|---|---|
| 5,380,485 A * | 1/1995 | Takahashi | B01J 19/004 422/106 |
| 2003/0137080 A1 | 7/2003 | Bouras et al. | |
| 2005/0001869 A1 | 1/2005 | Abernathy et al. | |
| 2006/0017916 A1* | 1/2006 | Clarke | A61J 3/00 356/300 |
| 2010/0128555 A1 | 5/2010 | Hughes et al. | |
| 2011/0252872 A1 | 10/2011 | Ding | |

FOREIGN PATENT DOCUMENTS

| | | |
|---|---|---|
| JP | 2001-324510 A | 11/2001 |
| JP | 2002-162404 A | 6/2002 |
| JP | 2003-028886 A | 1/2003 |
| JP | 2006-300843 A | 11/2006 |
| JP | 2011-227075 A | 11/2011 |
| JP | 2012-018126 A | 1/2012 |

OTHER PUBLICATIONS

International Search Report (PCT/ISA/210) mailed on Jun. 18, 2013, by the Japanese Patent Office as the International Searching Authority for International Application No. PCT/JP2013/002798.

Written Opinion (PCT/ISA/237) mailed on Jun. 18, 2013, by the Japanese Patent Office as the International Searching Authority for International Application No. PCT/JP2013/002798.

Extended European Search Report issued in corresponding European Patent Application No. 13781117.0-1371 / 2843419 PCT/JP2013/002798, dated Feb. 25, 2016 (16 pages).

* cited by examiner

DISCHARGE SYSTEM AND METHOD OF DISCHARGE BY A DISCHARGE SYSTEM

TECHNICAL FIELD

The present invention relates to a discharge system and to a method of discharging a liquid material onto a target using a discharge system.

BACKGROUND ART

Japanese Laid-Open Patent Publication No. 2001-324510 (hereinafter "Document 1) discloses the provision of a highly convenient variable discharge amount liquid dispensing apparatus and variable discharge amount automatic separating system that are capable of setting the added amounts of samples at desired values in a variety of ways such as in each well, in each column, or in each row, and by doing so are both highly precise and accurate and have general purpose applicability. To do so, Document 1 discloses that a pump for drawing liquid sample stored in a tank is provided corresponding to each pipette and the pumps are controlled by a control unit so that predetermined amounts of the liquid sample are individually introduced into the wells in the respective columns or the respective rows by the respective pipettes.

DISCLOSURE OF THE INVENTION

Technologies (patterning technologies) that utilize ink jet technology developed as a printing apparatus to draw with and/or apply a liquid material including paint, such as an ink, and a chemicals, such as a reagent, by discharging the liquid material are in use or are being investigated for use in a variety of fields such as printing, the manufacturing of image devices such as liquid crystal panels, the manufacturing of semiconductors including DNA chips, and immunological tests. When discharging various liquid materials onto a target, it is important to discharge with the desired discharge amounts.

One aspect of the present invention is a discharge system including: a discharge head that discharges a liquid material onto a target from a nozzle opening that is communicated with a cavity by changing an internal pressure of the cavity using an actuator; a state estimating unit that estimates a state of the liquid material by sucking the liquid material from a first vessel holding the liquid material into the cavity via the nozzle opening; and a driving condition setting unit that sets conditions for driving the actuator according to the estimated state of the liquid material.

With ink jet technology, if the conditions for discharge are set, it is possible to discharge a liquid material with favorable reproducibility and to manage the discharge amount of the liquid material on a droplet level. In this discharge system, by sucking a liquid material whose state is unclear and estimating the state of the liquid material, it is possible to set conditions for driving the actuator according to the estimated state of the liquid material. Accordingly, it is possible to provide a discharge system that is likely to discharge a desired discharge amount of liquid material, even for an unknown liquid material.

It is desirable for the state estimating unit to include a viscosity estimating unit that estimates a viscosity of the liquid material according to a suction amount and a suction time when applying a predetermined pressure and for the driving condition setting unit to include a waveform control unit that controls a voltage applied to the actuator according to the estimated viscosity of the liquid material. With a liquid material whose viscosity is unclear, by estimating the viscosity, it is possible to set a driving voltage that is suited to discharging a desired discharge amount.

It is desirable for the discharge system to include a liquid level detecting unit that detects the liquid level of the liquid material when the discharge head has sucked the liquid material and for the state estimating unit to include a unit that estimates a state of the liquid material according to the liquid level moving or reaching a predetermined position. It is desirable for the liquid level detecting unit to include a sensor that detects the liquid level that has reached the predetermined position.

In addition, it is desirable for the state estimating unit to include a unit that estimates the state of the liquid material according to a change in weight of the first vessel. To estimate the state according to a change in weight of the first vessel, it is desirable to precisely measure the weight of the first vessel. It is desirable for the discharge system to further include: a weight measuring unit that measures the weight of a vessel group including the first vessel and of the liquid material held in the vessel group; and a first discharge amount confirming unit that measures, using the weight measuring unit, a change in weight when the discharge head has sucked from any vessel in the vessel group and a change in weight when the discharge head has discharged into any vessel in the vessel group and identifies or confirms the discharge amount of the discharge head. With ink jet technology, since the discharge amount per droplet has high reproducibility, by identifying the weight in advance, it is possible to manage the discharge amount by managing the number of droplets without managing the weight itself. In this discharge system, it is possible to confirm the amount per single droplet from the number and amount of droplets that have been discharged and to manage the discharge amount onto the target according to the number of droplets.

It is also desirable for the discharge system to include a second discharge amount confirming unit that measures, using the weight measuring unit, a change in weight when the discharge head has discharged into any vessel in the vessel group after discharging onto the target and confirms the discharge amount of the liquid material discharged onto the target. By measuring the weight of any vessel out of the vessel group, it is possible to detect the discharge amount of the liquid material onto the target. In this discharge system, since the discharge amount is managed using the number of droplets discharged onto the target, by detecting, after discharge onto the target, the number of droplets and discharge amount discharged onto the target, it is possible to confirm the amount discharged onto the target.

It is desirable for the discharge system to further include: a weight measuring unit that measures the weight of a vessel group including the first vessel and of the liquid material held in the vessel group; and a second discharge amount confirming unit that measures, using the weight measuring unit, a change in weight when the discharge head has sucked from any vessel in the vessel group and a change in weight when the discharge head has discharged into any vessel in the vessel group after discharging onto the target, and identifies the discharge amount of the liquid material discharged onto the target.

It is desirable for the discharge system to further include: an image pickup unit that picks up an image of droplets discharged from the nozzle opening into any vessel in the vessel group; and a reproducibility checking unit that checks reproducibility of a discharge state of the droplets by comparing images recorded by the image pickup unit.

It is desirable for the discharge system to further include a table moving unit that moves a table on which the target is placed relative to the head unit so that the target is positioned below the discharge head, and for the image pickup unit to move to a position that picks up images of the droplets in cooperation with movement of the table by the table moving unit.

It is desirable for the vessel group to be mounted on the weight measuring unit, and for the discharge system to further include a conveying unit that moves the weight measuring unit relative to the discharge head.

It is possible for the discharge system to further include a lock unit that restricts movement between the weight measuring unit relative and the discharge head.

It is desirable for the lock unit to include: a lock rod that moves up and down in cooperation with raising and lowering of the discharge head; and a lock plate operable to restrict, when the discharge head has been inserted in the first vessel, the movement of the lock rod in a horizontal direction and to fix a position of the discharge head.

The discharge system may include a plurality of the discharge heads, the state estimating unit may include a unit that estimates states of a plurality of liquid materials held in a plurality of vessels respectively by sucking the plurality of liquid materials using the plurality of discharge heads respectively, and the driving conditions setting unit may include a unit that sets conditions for driving the respective actuators according to the respective estimated states of the liquid materials.

Another aspect of the present invention is a method of discharging a liquid material onto a target using a discharge system, the discharge system including a discharge head that discharges a liquid material on to the target from a nozzle opening that is communication with a cavity by changing an internal pressure of the cavity using an actuator and a control unit that controls the actuator, the method including: estimating, with the control unit, a state of the liquid material by sucking the liquid material from a first vessel holding the liquid material into the cavity via the nozzle opening; and setting conditions for driving the actuator according to the estimated state of the liquid material.

It is desirable for the estimating of the state to include estimating a viscosity of the liquid material according to a suction amount and a suction time when applying a predetermined pressure, and for the setting of the conditions for discharge to include controlling a voltage applied to the actuator according to the estimated viscosity of the liquid material.

DETAIL DESCRIPTION

Figure 1:
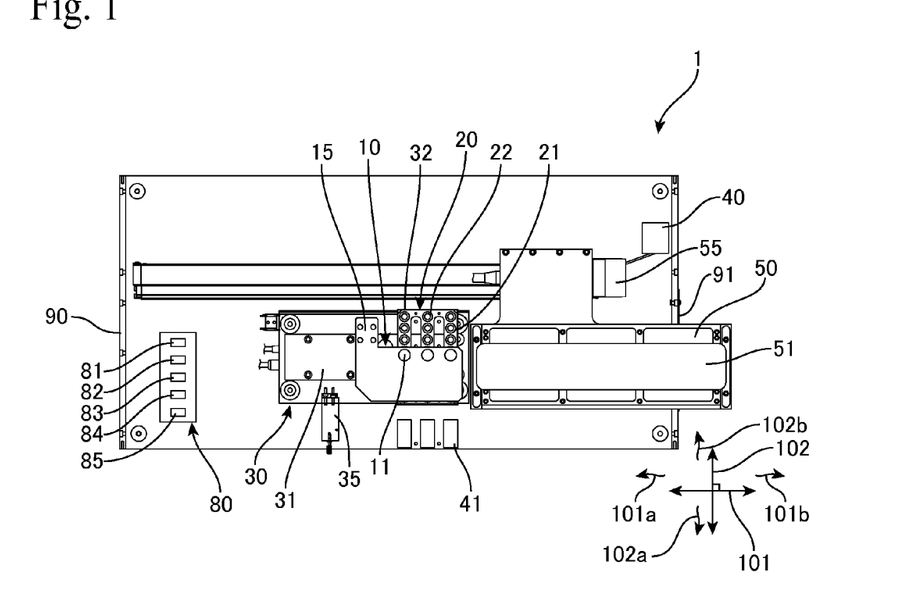
FIG. 1 is a top view of a discharge system.
Figure 2:
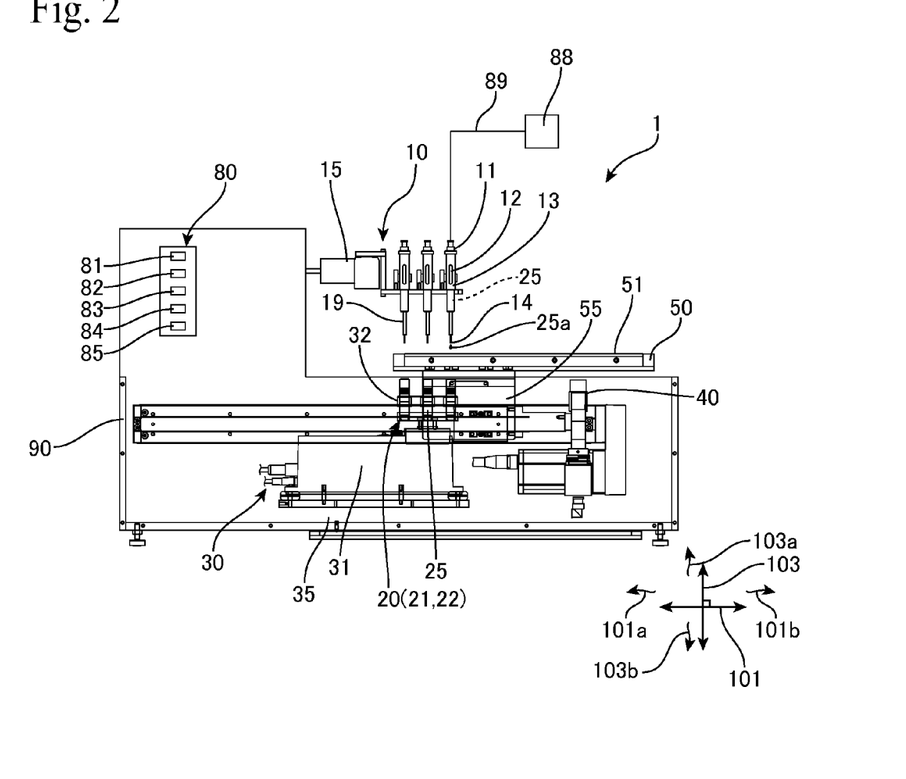
FIG. 2 is a front view of the discharge system from the front.

FIG. 1 and FIG. 2 show the overall configuration of a discharge system according to the present invention by way of views when looking from different directions. FIG. 1 is a view when looking at the discharge system from above and FIG. 2 is a view when looking at the discharge system from in front. This discharge system (or drawing system, applying system, discharge apparatus, immunochromatography dispenser apparatus) 1 includes a head unit 10 including a discharge head 11 that discharges a liquid material (such as a liquid, antibody, antigen, protein, DNA solution, reagent, or analyte) 25 onto a target (membrane, cellulose film) 51, a weight measuring unit 30 including an electronic weighing machine 31 that measures the weight of a vessel group (liquid bottle group) 20 from which the liquid material 25 is sucked or into which the liquid material 25 is discharged, and a control unit 80 that controls the head unit 10 and the weight measuring unit 30. The head unit 10, the weight measuring unit 30, and the control unit 80 are housed inside a housing 90. The vessel group (liquid bottle group) 20 may be tubes or chips made of resin.

The head unit 10 includes three discharge heads 11 that are aligned in a first direction (X direction, left-right direction) 101, actuators (piezo elements, piezoelectric elements) 12 that cause variation (change) in the internal pressures (internal volumes) of cavities (pressure chambers) 13 of the discharge heads 11, and a head moving unit (motors) 15 that moves the discharge heads 11 in a second direction (Y direction, front-rear direction) 102 and a third direction (Z direction, up-down direction). The respective discharge heads 11 are nozzle types that include independent cylindrical members (nozzles) 19 made of glass and are suction (draw)-type heads where the front ends of the cylindrical members 19 extend narrowly to end in nozzle openings 14, with such nozzle openings 14 being respectively inserted into vessels 20 and being capable of sucking in the liquid material 25. Note that the head unit 10 may include four or more discharge heads 11 and the respective discharge heads 11 do not need to be aligned in a row in the left-right direction 101 and as one example may be laid out so that the positions in the front-rear direction 102 are staggered. Also, the first direction 101, the second direction 102, and the third direction 103 are respectively perpendicular.

The weight measuring unit 30 includes the electronic weighing machine 31, a tray 32 mounted on the electronic weighing machine 31, and a group of vessels (liquid bottle group) 20 having twenty-four vessels arranged on the tray 32. The twenty-four liquid bottles 20 are laid out in a matrix with three columns (rows) in the left-right direction 101 and eight columns (rows) in the front-rear direction 102, and include twenty-one vessels assigned as the first vessels 21 disposed in the first to seventh columns from the front 102a and three vessels assigned as the second vessels 22 disposed in a single column at the very rear 102b. The first vessels 21 are vessels where different liquid materials 25 are stored in each column in the left-right direction 101 and the second vessels 22 are vessels for discharging (expelling, ejecting, exhaling) the liquid material 25, with no liquid material 25 being held in the second vessels 22 when the vessels are initially set.

In this discharge system 1, when an instruction (suction signal) for sucking the liquid material 25 is outputted from the control unit 80, the head moving unit 15 moves the discharge heads 11 in the front-rear direction 102 to dispose the discharge heads 11 at a position that is above 103a of the first vessels 21 and lowers the nozzle openings 14 at the front ends of the discharge heads 11 downward 103b to insert the nozzle openings 14 into the liquid material 25 in the first vessels 21. A pressure control unit 88 that has received the suction instruction applies negative pressure via tubes 89 to the discharge heads 11 so that the liquid material 25 is sucked (siphoned) from the first vessels 21 into the cavities 13 and the tubes 89. It is also possible to use a configuration where a vessel or receiver (not shown) is provided between the discharge heads 11 and the pressure control unit 88 and the liquid material 25 is sucked up into such vessel. When an instruction (discharge signal) for discharging the liquid material 25 has been outputted from the control unit 80, the head moving unit 15 raises the discharge heads 11 upward 103a to remove the nozzle openings 14 at the front ends from the first vessels 21, and moves the discharge heads 11 in the front-rear direction 102 to dispose the discharge heads 11 at desired positions (for example, the position of the target 51 or above 103a of the second vessels 22). A driver (not shown) that has received the discharge instruction drives the piezo elements 12 of the discharge heads 11 and by expanding/contracting and/or deforming the piezo elements 12 to cause variations (change) in the internal pressure of the cavities 13, the liquid material 25 is discharged as droplets 25a from the nozzle openings 14 that are communication with (connected to) the cavities 13.

For the discharge system 1, as the initial state, the first vessels 21 above the electronic weighing machine 31 may be filled or not filled with liquid materials 25. In the cases where the first vessels 21 are not filled with liquid materials 25, empty first vessels 21 and second vessels 22 are set on the electronic weighing machine 31. Here, if the weight measuring unit 30 measures the total weight of the component members of the vessels 20 and the like on the electronic weighing machine 31 in a state where the first vessels 21 are empty and then measures the total weight in the same way in a state where liquid materials 25 have been set in the first vessels 21, it is possible to know the weight of the liquid materials 25 that have been set. By using this total weight of the set liquid material 25 whenever the discharge weight of a liquid material 25 discharged onto a membrane (target) 51 and/or the weight expelled (ejected, exhaled) during cleaning, the amount that adheres to the nozzle openings 14 and is wiped away using a wiper or a porous body, and the like are subsequently calculated, it is possible to calculate the effective remaining amount. Alternatively, when measurement starts in a state with the liquid material 25 already set in the first vessels 21, by using the weight measuring unit 30 to measure the change in weight when the discharge heads 11 have sucked from the first vessels 21, the change in weight when the discharge heads 11 have discharged into the second vessels 22, and the change in weight when the discharge head 11 have discharged into the second vessels 22 after discharging on the target 51, and the like, it is possible to measure the weight of the liquid material 25 that moves between the first vessels 21, the second vessels 22, and the discharge heads 11. Note that it is possible to measure the change in weight and the like in the same way by discharging the liquid material 25 sucked from the first vessels 21 into the first vessels 21 themselves, not the second vessels 22.

With the weight measuring unit 30, the weight of the first vessels 21 and the second vessels 22 is constantly monitored. This means that the weight of the liquid material 25 sucked up by the discharge heads 11 from the first vessels 21 is known. In addition, if a predetermined number of droplets 25a are discharged by the discharge heads 11 into the first vessels 21 or the second vessels 22, the increase in weight due to each discharge will be known. With an ink jet, the discharge amount of each droplet has high reproducibility. This means that if the increase in weight is divided by number of discharges, the discharge amount of each droplet can be precisely identified and it will be possible to subsequently manage the weight by managing the number of droplets. For this reason, as examples the weight of the liquid material 25 set in the first vessels 21, the weight of the liquid material 25 sucked into the cavities 13 of the discharge heads 11, the weight of the liquid material 25 discharged from the discharge heads 11, the weight of the liquid material 25 remaining in the first vessels 21 (the second vessels 22), and the weight of the liquid material 25 remaining in the cavities 13 of the discharge heads 11 can all be calculated (measured, detected). In addition, since it is possible to calculate the remaining weight in the second vessels 22 that hold the liquid material 25 expelled from the discharge heads 11, it is possible to estimate the liquid level height of the liquid material 25 in the second vessels 22 without relying on image processing, a light beam sensor or the like. This means that it is possible to monitor the total weight of the liquid material 25 expelled from the discharge heads 11 and to avoid the liquid material 25 overflowing from the second vessels 22.

The discharge system 1 also includes a conveying unit 35 that moves the weight measuring unit 30 in the left-right direction 101 with respect to the head unit 10, a lock unit that restricts the movement of the weight measuring unit 30 in the left-right direction 101 with respect to the head unit 10, a table moving unit 55 that moves a table (stage) 50 on which the target 51 is placed in the left-right direction 101 with respect to the head unit 10 to position the target 51 below 103b of the discharge heads 11, and an image pickup unit 40 that moves in coordination with movement of the table 50 by the table moving unit 55 to a position facing the second vessels 22 and picks up images of the droplets 25a (liquid material 25) discharged into the second vessels 22.

The image pickup unit 40 is typically a camera equipped with an image pickup element such as a CCD or a CMOS and an optical lens. The images acquired by the camera 40 are sent to the control unit 80 and subjected to recording (history management) and image processing, and by recognizing and comparing the state of the droplets 25a, for example, the flying form (flying direction, discharge form, discharge state) of the droplets 25a discharged into the second vessels 22, it is possible to confirm or check the reproducibility of the flying form and to recognize fine particles (granules, cells) and the like included in the droplets 25a. Three flashes 41 are disposed in front 102a of the three second vessels 22 so as to face the second vessels 22 in the front-rear direction 102.

The control unit 80 of the discharge system 1 includes general-purpose resources for a computer, such as a CPU and memory, and controls the head unit 10, the weight measuring unit 30, the conveying unit 35, the table moving unit 55, the image pickup unit 40, the pressure control unit 88, and the like in accordance with a program (program product) stored in memory such as a RAM. The control unit 80 may be a control apparatus that uses an ASIC, LSI, or other integrated circuit. The respective units (functions) of the control unit 80 described below are implemented in the control unit 80 by programs or appropriate circuits. The respective units of the control unit 80 are also capable of being realized at a host apparatus such as a personal computer that is a host of the discharge system 1.

The control unit 80 includes a viscosity estimating unit (state estimating unit) 81 that estimates the viscosity (states, characteristics, properties) of each liquid material 25 by sucking the liquid material 25 into the cavities 13 from the first vessels 21 via the nozzle openings 14, a waveform control unit (pressure control unit, driving condition setting unit) 82 that controls the conditions for driving the piezo elements 12 according to the estimated viscosity (state) of the liquid material 25, for example, controlling (for each liquid material 25, that is, for each nozzle) the voltage, pulse width, and pulse waveform applied to the piezo element 12, a reproducibility checking unit 83 that confirms or checkes the reproducibility of the discharge state (flying form) of the droplets 25a for each liquid material by comparing images recorded by the image pickup unit 40 for each nozzle, a first discharge amount confirming unit 84 that identifies or confirms, for each liquid material, the discharge amount and discharged number of droplets of the liquid material 25 discharged into the second vessels 22 using the weight measuring unit 30 and calculates and/or identifies the weight of each droplet for each nozzle, and a second discharge amount confirming unit 85 that confirms, for each liquid material, the discharge amount and discharged number of droplets of the liquid material 25 discharged into the second vessels 22 after discharging onto the target 51 using the weight measuring unit 30 and calculates and/or confirms the weight of each droplet for each nozzle.

Figure 3:
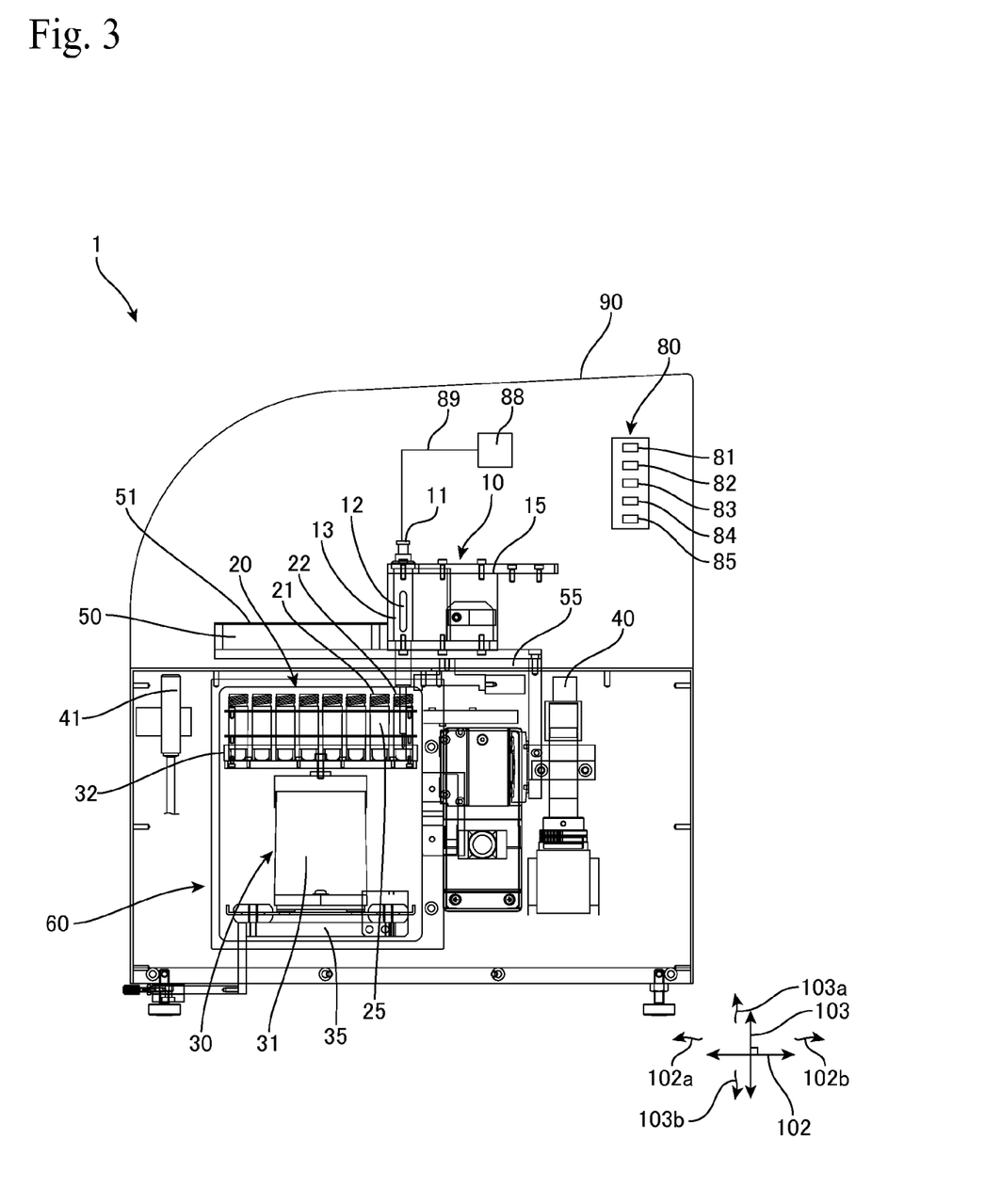
FIG. 3 is a right side view of the discharge system when a discharge head is on suction.

FIG. 3 shows how the discharge head 11 suck the liquid material 25 from the first vessels 21 when looking at the discharge system 1 from the right side 101b. The viscosity estimating unit 81 of the control unit 80 estimates the viscosity of the liquid material 25 sucked by the discharge heads 11 into the cavities 13 or the tubes 89 or vessel (not shown) positioned upstream of the cavities 13.

One example of a method of estimating the viscosity of the liquid material 25 is to estimate the viscosity of the liquid material 25 according to the suction amount a and the suction time t of the liquid material 25. Normally, since the form of a nozzle that includes a nozzle opening will differ from discharge head to discharge head, the fluid resistance for a liquid material that is pressed out from the cavity to the nozzle opening will differ between discharge heads. This means that the amount of discharged liquid material will differ between discharge heads even with the same discharge conditions and that it is not easy to discharge the liquid material with a desired discharge amount. In addition, when discharging an unknown liquid material for which the state (characteristics, properties), including the viscosity, is unclear, it is even more difficult to carry out stabilized discharge with a desired discharge amount.

With the present invention, a liquid material (liquid) whose viscosity has been known in advance is sucked into each discharge head in an environment with a predetermined temperature, pressure, and time, the suction amount in such case is measured, such measurement is carried out for a plurality of viscosities, and data such as the suction amount and suction time measured for each viscosity is recorded in advance in a memory provided in each discharge head as unique values (head data) of such discharge head. When the discharge heads 11 in which such head data has been written are installed in the discharge system 1, the viscosity estimating unit 81 of the control unit 80 reads the head data (head ID) for each discharge head 11 and, based on the head data, produces (generates) an approximation function f that estimates the viscosity X of a liquid material 25 as a function of the suction amount a, the suction time t, or the suction amount a and the suction time t. Accordingly, with the viscosity estimating unit 81, by substituting the suction amount a measured by the weight measuring unit 30, the suction time t, or the suction amount a and the suction time t into the approximation function f, it is possible to estimate the viscosity X, even for an unknown liquid material 25.

The waveform control unit 82 of the control unit 80 controls the piezo elements 12 according to a voltage or voltage pattern that is suited to discharging a liquid material 25 with the viscosity X estimated by the viscosity estimating unit 81. This means that even if a liquid material 25 whose state is unclear has been sucked into the discharge heads 11, the viscosity estimating unit 81 will estimate the viscosity of such liquid material 25 and the waveform control unit 82 will be automatically set at an optimal driving voltage and pulse width, pulse waveform (discharge conditions) according to the estimated viscosity. Accordingly, it is possible to provide the discharge system 1 that is capable of stably discharging with the desired discharge amount, even for an unknown liquid material 25. The voltage or voltage pattern suited to discharging the liquid material 25 with the viscosity X may be set based on a function of the viscosity X of the liquid material 25 estimated by the viscosity estimating unit 81 and droplet speed V.

With this discharge system 1, after the liquid material 25 has been sucked from the first vessels 21, when the discharge head 11 are raised and are pulled up into the atmosphere from the first vessels 21, there is the possibility of the liquid material 25 adhering to the periphery of the nozzle openings 14. If the weight of the first vessels 21 before the liquid material 25 is sucked up (i.e., the total weight of the first vessels 21 and the liquid material 25) is W1, the weight of the first vessels 21 after the liquid material 25 is sucked up is W2, and the weight (adhering weight) of the liquid material 25 adhering to the periphery of the nozzle openings 14 without being sucked into the cavities 13 is b, the weight a of the liquid material 25 that is actually sucked into the cavities 13 can be found according to the Equation (1-1) below.

$$a = W1 - (W2 + b) \tag{1-1}$$

One example of a method of finding the adhering weight b of the liquid material 25 is to install an absorbent body (not shown) that absorbs the liquid material 25 on the electronic weighing machine 31 of the weight measuring unit 30, to press the absorbent body onto the nozzle openings 14 to absorb the adhering liquid material 25 into the absorbent body, and then measure the weight. That is, if the weight after an absorbent set on the electronic weighing machine 31 has absorbed the adhering liquid material 25 is W2' (W2'=W2+b), it is possible to find the weight a of the liquid material 25 actually sucked into the cavities 13 according to the equation (2-1) below.

$$a = W1 - W2' \tag{2-1}$$

Another example of a method of finding the adhering weight b of the liquid material 25 is to experimentally find the adhering weight b of the liquid material 25 by carrying out a test multiple times in advance. That is, if the average adhering weight of the adhering weight b found by a plurality of experiments is b', the weight a of the liquid material 25 actually sucked into the cavities 13 can be found according to the equation (2-2) below.

$$a = W1 - (W2 + b') \qquad (2\text{-}2)$$

Another example of a method of finding the adhering weight b of the liquid material 25 measures the weight of the liquid material 25 of the first vessels 21 in advance using the weight measuring unit 30, then sucks the liquid material 25 with negative pressure using the pressure control unit 88, measures the weight of the liquid material 25 after suction using the weight measuring unit 30, and finds the suction amount W3 according to such difference. After this, positive pressure is applied using the pressure control unit 88 to expel (exhaled, ejected) all of the liquid material 25 into the second vessels 22 and the weight W4 of the expelled liquid material 25 is measured using the weight measuring unit 30. By doing so, once "W3 −W4"has been found, it is possible to set the result as the adhering weight b of the liquid material 25 that adheres to the periphery of the nozzle openings 14. In the above description, instead of expelling into the second vessels 22, it is also possible to find the adhering weight b in the same way by expelling into the original first vessels 21.

In addition, the discharge system 1 includes a lock unit 60 that restricts the movement of the weight measuring unit 30 in the left-right direction 101 during suction, that is, while the discharge heads 11 are inserted into the first vessels 21.

Figure 4:
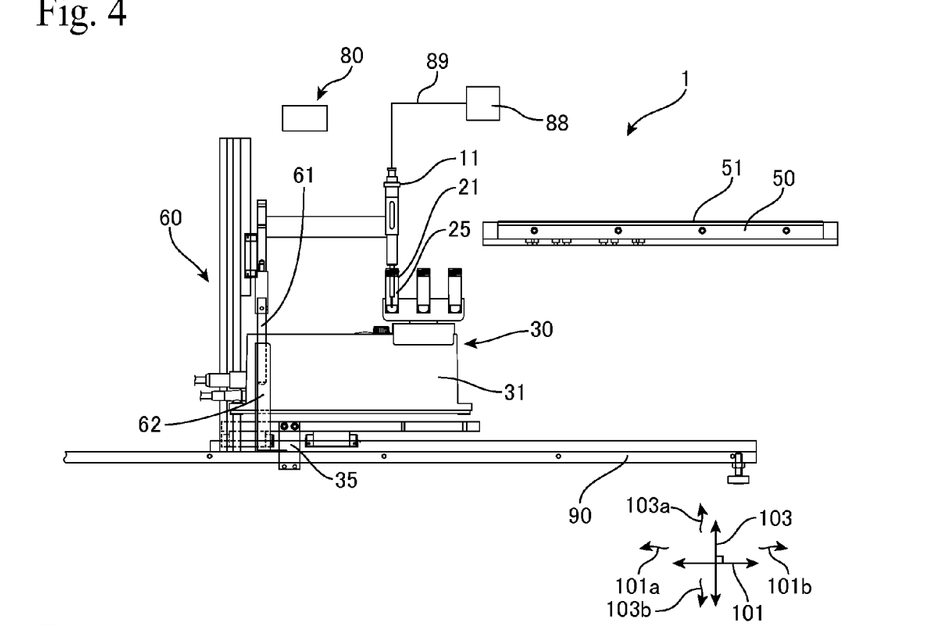
FIG. 4 is a front view of the discharge system showing how a lock unit is locked.

FIG. 4 shows how the lock unit 60 is locked by way of a view looking at the discharge system 1 from the front side 102a. The lock unit 60 includes a lock rod 61 that moves up and down in coordination with raising and lowering of the discharge heads 11 and a lock plate 62 that restricts the movement of the lock rod 61 in the horizontal direction (left-right direction) 101 and fixes the position of the discharge heads 11 when the discharge heads 11 have been inserted into the first vessels 21. The lock plate 62 is provided or fitted on a side surface of the electronic weighing machine 31 and fixed by the lock rod 61 so that the weight measuring unit 30 does not move to the right 101b during suction by the discharge heads 11. Hence, it is possible, during suction by the discharge head 11, to prevent movement in the left-right direction 101 of the first vessels 21 set on the electronic weighing machine 31. Accordingly, it is possible to suppress damage to the discharge heads 11, such as the breakage of the nozzles, due to the discharge heads 11 interfering (colliding) with the first vessels 21 and in addition to suppress leakage of the liquid material 25 due to the first vessels 21 tilting (falling over) or the like.

Note that the lock unit 60 may include a lock rod 61 that moves up and down in coordination with raising and lowering of the discharge heads 11 and a lock hole (not shown) into which the lock rod 61 is inserted and fixes the position of the discharge heads 11 when the discharge heads 11 are positioned above 103a the first vessels 21. Since it is possible to lock the discharge heads 11 when positioned above 103a of the first vessels 21, it is possible to prevent, when the discharge heads 11 are not positioned above the first vessels 21, the discharge heads 11 from being lowered and interfering with the first vessels 21 or the like, which can damage the discharge heads 11 and/or the first vessels 21.

Figure 5:
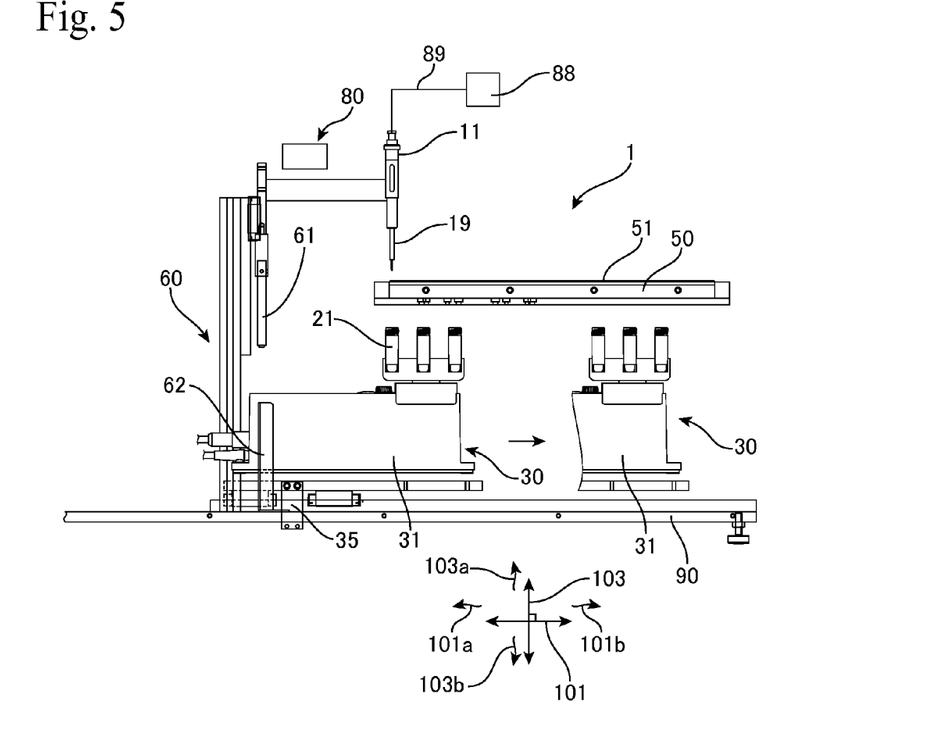
FIG. 5 is a front view of the discharge system showing a state where the locking of the lock unit is released.
Figure 6:
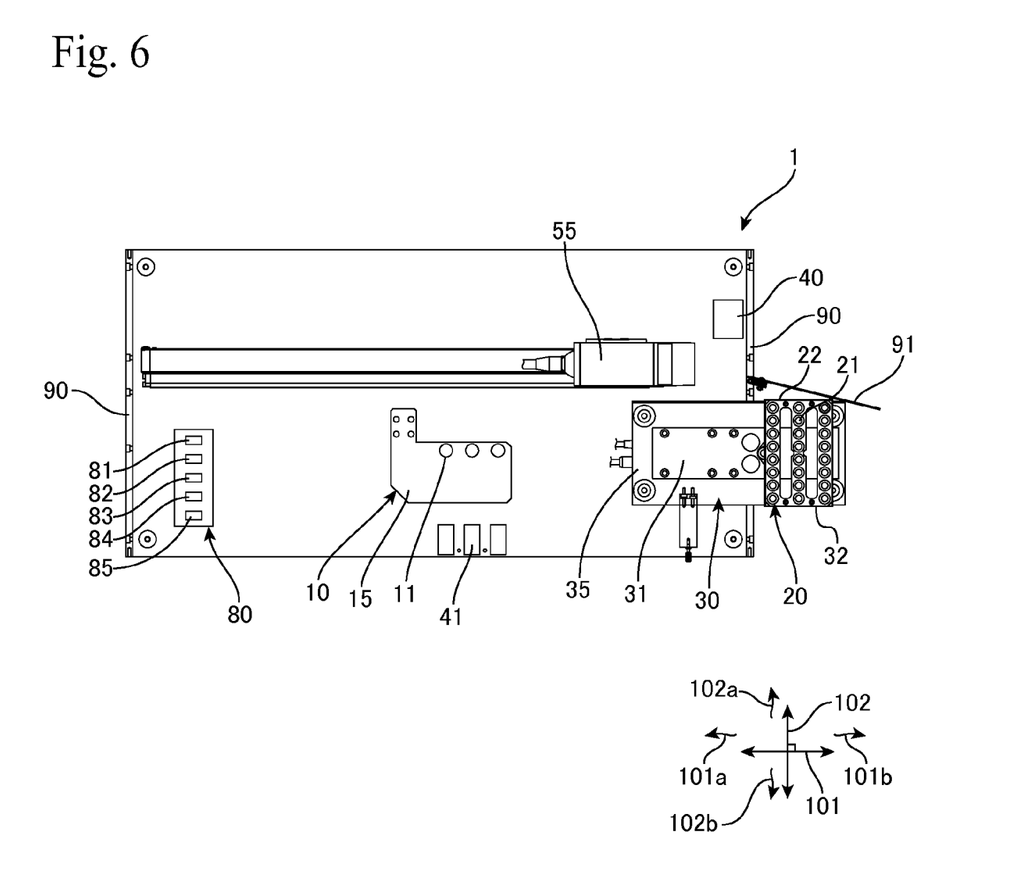
FIG. 6 is a top view of the discharge system showing a state where the locking of the lock unit is released.

FIG. 5 shows a state where the locking of the lock unit 60 is released, by way of a view when looking at the discharge system 1 from the front side 102a. FIG. 6 shows a state where the locking of the lock unit 60 is released, by way of a view (a view that omits the table 50) when looking at the discharge system 1 from above (top side) 103a. When suction by the discharge head 11 ends and the head moving unit 15 raises the discharge heads 11 to remove the discharge heads 11 from the first vessels 21, the lock rod 61 is raised in cooperation with the raising of the discharge heads 11. This means that when the discharge heads 11 are removed from the first vessels 21, the lock is removed and the weight measuring unit 30 is pulled out toward the right side 101b. Accordingly, the weight measuring unit 30 for which the lock has been removed is moved to the right 101b by the conveying unit 35 on the rails that extend in the left-right direction 101, and can be attached and detached from the housing (chassis, case, housing) 90 to the outside via a door 91. It is possible to replace the liquid bottles 20 (the tray 32) without removing the weight measuring unit 30 in the upward direction 103a. Note that in the present embodiment, the locking is released when the lock rod 61 is raised by around 40 mm.

Figure 7:
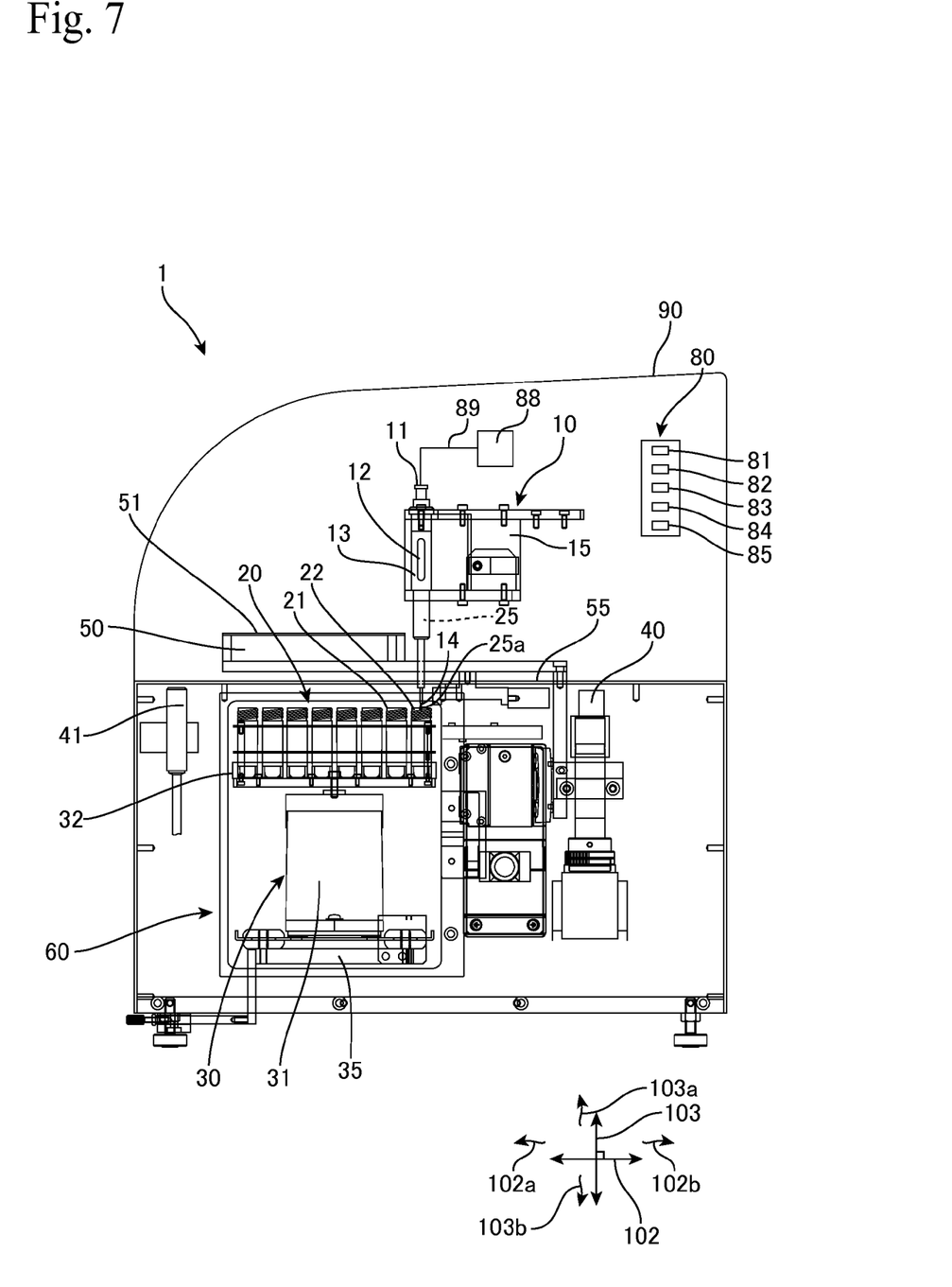
FIG. 7 is a right side view of the discharge system showing how the discharge heads discharge the liquid material into second vessels.

FIG. 7 shows how the discharge heads 11 discharge the liquid material 25 into the second vessels 22 by way of a view looking at the discharge system 1 from the right side 101b. In this discharge system 1, when an instruction for discharging the liquid material 25 to the second vessels 22 is outputted from the control unit 80, the head moving unit 15 moves the discharge heads 11 in the front-rear direction 102 and the up-down direction 103 so that the discharge heads 11 are disposed at positions above 103a of the desired second vessels 22. Images of the droplets 25a discharged from the discharge heads 11 into the second vessels 22 are picked up (acquired, taken) by the camera 40 and the flashes (strobe light) 41 disposed on respective sides of the second vessels 22 in the front-rear direction 102.

The reproducibility checking unit 83 of the control unit 80 confirms or checks the reproducibility or repeatability of the flying form (discharge state) of the droplets 25a by comparing the images recorded by the camera 40. Accordingly, since it is possible to confirm the reproducibility of the flying form (flying direction) of the droplets 25a by comparing images of the droplets 25a discharged into the second vessels 22, it is possible to carry out discharging of the liquid material 25 in a stable discharge state. In addition, in place of comparing images, by using a plurality of images of the droplets 25a where the light emission (flash) timing of the strobe light 41 is changed, it is also possible to measure the droplet speed of the droplets 25a and to confirm reproducibility with regard to a speed of the droplets 25a inputted in advance. If there is no reproducibility or no repeatability for the flying form and/or flying speed of the droplets 25a, or if it is determined that there is a problem with the flying form, there is the possibility that the liquid material 25 will not reach the desired target 51. Accordingly, in the discharge system 1, cleaning is carried out such as by removing foreign matter and the like adhering to the periphery of the nozzle openings 14 of the discharge heads 11 using a wiping unit (not shown) and moving the discharge heads 11 to a disposer (not shown) and test discharging the droplets 25a. If the problem is not solved by doing so, cleaning is carried out by applying positive pressure to the discharge heads 11 using the pressure control unit 88 so that bubbles inside the cavities 13 and in the flow paths are expelled to the outside together with the liquid material 25.

The first discharge amount confirming unit 84 of the control unit 80 measures, using the weight measuring unit 30, the change in weight when the discharge heads 11 have sucked from the first vessels 21 and the change in weight when the discharge heads 11 have discharged into the second vessels 22 and confirms (identifies) the discharge amount of the liquid material 25 discharged into the second vessels 22.

By this unit, it is possible to confirm whether a desired discharge amount of liquid material 25 will be discharged before the liquid material 25 is discharged onto the target 51. That is, in immunochromatography dispensing applications, it is important to correctly manage the amount of the reagent 25 seeped into the membrane that is the target 51, and by carrying out discharge into the second vessels 22 according to the same discharge conditions as the real discharge onto the target 51, it is possible to simulate the amount of the reagent 25 consumed by the real discharge.

Figure 8:
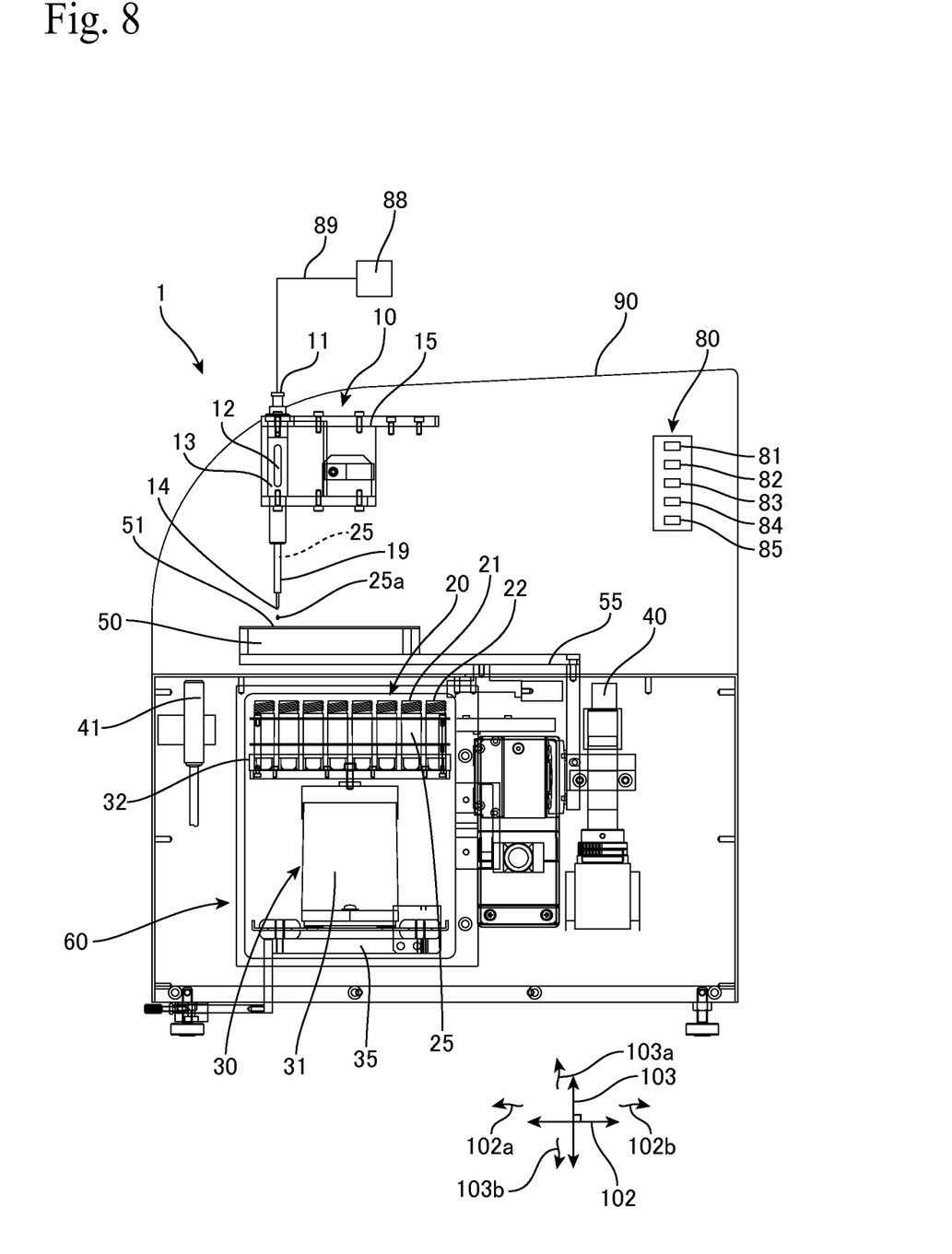
FIG. 8 is a right side view of the discharge system showing how the discharge heads discharge the liquid material onto a target.

FIG. 8 shows how the discharge heads 11 discharge the liquid material 25 onto the target 51 by way of a view where the discharge system 1 is viewed from the right side 101b. In the discharge system 1, when an instruction for discharging the liquid material 25 onto the target 51 has been outputted from the control unit 80, the discharge heads 11 are moved in the front-rear direction 102 and the up-down direction 103 by the head moving unit 15 to dispose or set the discharge heads 11 at a position above 103a of the target 51 and the table 50 on which the target 51 has been placed is moved by the table moving unit 55 in the left-right direction 101 so that the liquid material 25 is drawn (discharged) in lines on the target 51.

The second discharge amount confirming unit 85 of the control unit 80 measures, using the weight measuring unit 30, changes in weight after the discharge heads 11 have discharged into the second vessels 22 after discharging onto the target 51 and confirms or identifies the discharge weight of the liquid material 25 discharged onto the target 51. This means that after the liquid material 25 has been discharged onto the target 51, it is possible to confirm whether the desired discharge amount of the liquid material 25 was discharged.

In the discharge system 1, if it is determined that the desired discharge amount of the liquid material 25 was not discharged, bad marking that indicates that lines were drawn by abnormal discharge on the target 51 is carried out by a marking unit (not shown). By the system 1, it is not necessary to continually visually check the discharging of the liquid material 25 on the target 51 and it is possible to confirm whether discharging on the target 51 was properly carried out after discharging onto the target 51. Accordingly, it is possible to automatically carry out discharge tests of the liquid material 25 on the target 51 in an unmanned state and it is possible to determine whether the test results pass or fail by confirming the discharge amount after discharge, which makes it possible to manage the quality of the target 51. If it is determined that the results of the discharge test pass, the manufactured target 51, that is, the target 51 on which a desired discharge amount of the liquid material has been drawn may be unloaded by a loading/unloading unit (not shown). In addition, with the discharge system 1, when confirming the discharge amount using the first and second discharge amount confirming unit 84 and 85, since the control unit 80 switches off a heat dissipating fan (not shown), it is possible to carry out measurement of the discharge amount with high precision while suppressing vibrations.

Alternatively, it is also possible to determine whether the desired dispensing has been carried out either visually or by image processing by using a dispensing image pickup unit (not shown) equipped with a CCD camera and a lens to pick up, immediately below (below 103b) or in the periphery of the nozzle openings 14 of the discharge heads 11, images of the dispensed state on the surface of the dispensing medium such as the membrane 51 or, immediately after dispensing, lines formed by the liquid material 25 before the liquid material 25 seeps into the membrane 51. It is desirable for this dispensing image pickup unit (not shown) to be configured so as to be integrated with the head unit 10 and to be arranged so as to acquire images of the dispensing area diagonally from above. If a plurality of discharge heads 11 are provided, it is possible to provide the same number of dispensing image pickup units as discharge heads 11 or to make the discharge heads 11 movable and to dispose the dispensing image pickup unit directly below the nozzle opening 14 of the discharge head 11 for which image pickup is desired.

Figure 9:
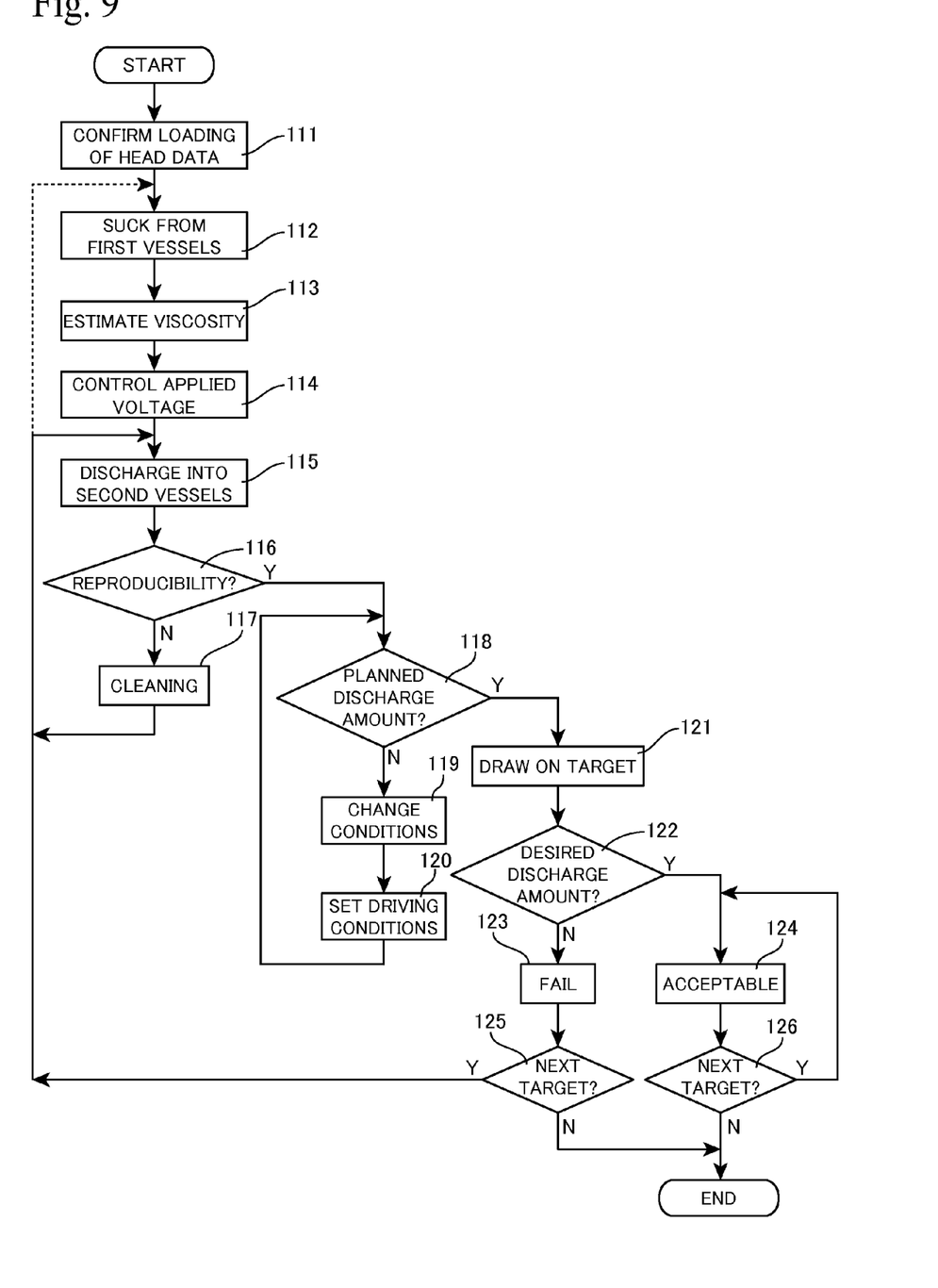
FIG. 9 is a flowchart of processing by a control unit.

FIG. 9 shows an overview of the processing of the control unit 80 of the discharge system 1 by way of the flowchart. In step 111, the control unit 80 confirms that the head data of the discharge head 11 mounted in the discharge system 1 has been loaded. The viscosity estimating unit 81 of the control unit 80 generates an approximation function f that estimates the viscosity X according to the suction amount a and the suction time t of the liquid material 25 based on the loaded head data.

In step 112, the control unit 80 moves and lowers the discharge heads 11 using the head moving unit 15 to insert the discharge heads 11 into the liquid material 25 in the first vessels 21, applies a negative pressure via the tubes 89 to the discharge heads 11 using the pressure control unit 88, and sucks (siphons) the liquid material 25 from the first vessels 21 into the cavities 13 and the tubes 89. Alternatively, a vessel (not shown) is provided between the discharge head 11 and the pressure control unit 88 and the liquid material 25 is sucked up into such vessel. In step 113, the viscosity estimating unit 81 estimates the viscosity X of the liquid material 25 according to the suction amount a of the liquid material 25 measured by the weight measuring unit 30 and the suction time t. In step 114, the waveform control unit 82 sets the voltage applied to the piezo elements 12 according to the estimated viscosity X. In step 115, the control unit 80 raises and moves the discharge heads 11 using the head moving unit 15 to position the discharge heads 11 above 103a the second vessels 22 and drives the piezo elements 12 using a driving voltage set by the waveform control unit 82 to discharge a predetermined number of droplets, for example 1,000 droplets, of the sucked-up liquid material 25 into the second vessels 22 and measures the weight. By doing so, the discharge amount per droplet is identified.

In step 116, the reproducibility checking unit 83 compares the images recorded by the camera 40 and/or the droplet speeds obtained from the images to confirm the reproducibility (repeatability) of the flying form (discharge state) of the liquid material 25 (the droplets 25a). On determining that there is no reproducibility, in step 117 the control unit 80 carries out cleaning using a wiping unit or the like and returns to step 115. Alternatively, as shown by the broken line, the processing may return to step 112 and be carried out again after a positive pressure has first been applied to the discharge heads 11 by the pressure control unit 88 to expel or exhale all of the liquid material 25 in the tubes 89 or inside the cavities 13 to the outside. If it is determined that there is reproducibility, in step 118 the first discharge amount confirming unit 84 uses the weight measuring unit 30 to confirm or identify the weight when a predetermined number of droplets of the liquid material 25 have been discharged into the second vessels 22. If the discharge amount into the second vessels 22 is not the planned value, in step 119 the control unit 80 carries out two-point correction and interpolation and extrapolation based on discharge results for discharge carried out by changing the discharge conditions, and in step 120, the driving conditions of the piezo elements 12 are reset before the processing returns to step 118.

If it has been determined that the discharge amount into the second vessels 22 is the planned value, in step 121 the control unit 80 moves the discharge heads 11 using the head moving unit 15 to dispose the discharge heads 11 at a position above 103a on the target 51 and moves the table 50 on which the target 51 is placed using the table moving unit 55 to draw (discharge) the liquid material 25 in lines on the target 51. In step 122, the second discharge amount confirming unit 85 confirms whether the desired discharge amount of the liquid material 25 was discharged onto the target 51 using the weight measuring unit 30. That is, after discharging onto the target 51, a predetermined number of droplets 25a are discharged onto the second vessels 22 again and it is confirmed that there is no change to the planned discharge amount confirmed in step 118. If, before and after discharge onto the target 51, there is no change in the discharge amount (per droplet), or there is a change that is within a predetermined error (tolerance), in step 124, it is determine whether the discharge amount onto the target 51 is correct and if necessary, a mark showing successful completion is added to the target. On the other hand, if the discharge amount has changed before and after discharge onto the target 51, in step 123 the control unit 80 determines that the discharge result of the liquid material 25 onto the target 51 is a fail, and if necessary, a mark showing a defect is added to the target.

In the discharge system 1, before discharging the liquid material 25 onto the target 51, by carrying out confirmation (diagnosis) of the reproducibility of the flying form using the reproducibility checking unit 83 and also carrying out confirmation (diagnosis) of the discharge amount using the first discharge amount confirming unit 84, it is possible to improve the probability of the desired discharge amount of the liquid material 25 being stably discharged toward the target 51. In addition, in the discharge system 1, after the liquid material 25 has been discharged onto the target 51, the reproducibility is checked and by storing the history, the reliability of the discharge results onto the target 51 is improved. Together with this, it is guaranteed that a target 51 of a predetermined quality has been manufactured according to the history or marks on the target 51. If there is a result is good (pass) in step 124, in step 126 it is confirmed whether there is a next target 51. If there is a next target 51, the processing returns to step 121 and manufactures the next target 51. If there is no next target 51, the processing ends. If there is a result is not good (fail) in step 123, in step 125 it is confirmed if there is a next target 51. If there is a next target 51, the processing returns to step 112 and readjustment is carried out from the setting of viscosity. Such processing is repeated until the targets end. In this example, the next target is successively loaded (supplied) onto the table 50 by a robot or the like (not shown).

Figure 10:
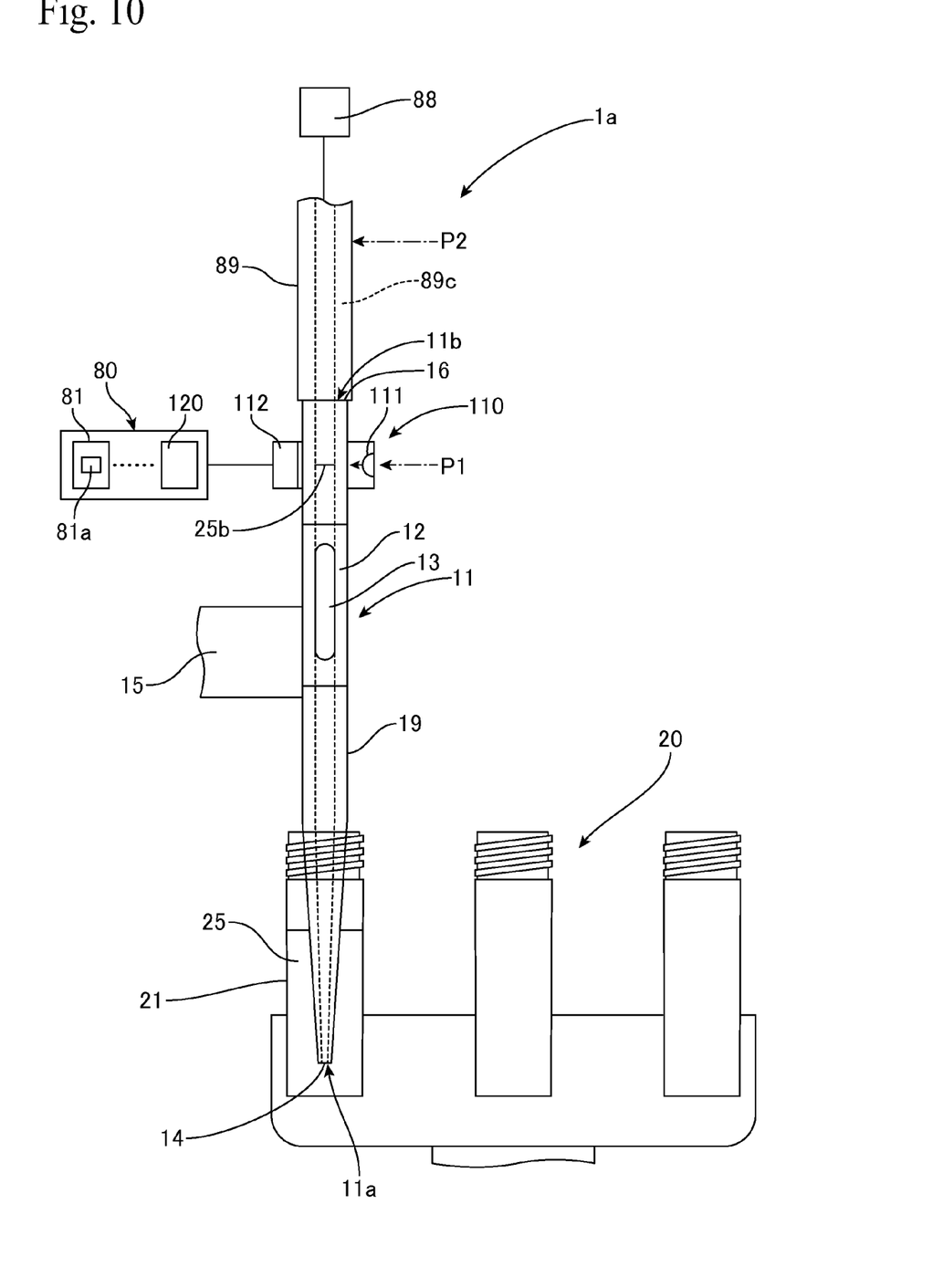
FIG. 10 is a view showing another example of measuring the suction time of a liquid material.

FIG. 10 shows another example of measuring the suction time t of the liquid material 25 in step 113 in FIG. 9. This discharge system 1a has the same configuration as the discharge system 1 and is also equipped with a liquid level detecting unit (sensor) 110 that detects a liquid level 25b of the liquid material 25 that has reached a predetermined position (first position) P1 when the liquid material 25 has been sucked by the discharge heads 11 and a suction time measuring unit (timer) 120 that starts suction of the liquid material 25 and measures the suction time t until detection of the liquid level 25b by the liquid level detecting unit 110.

Note that since the other configuration is the same as the embodiment described above, description thereof is omitted.

Each discharge head 11 has a translucent (transparent, semi-transparent) side wall portion 11c that is cylindrical (tube-shaped) and connects the nozzle opening 14 formed at the front end 11a of the cylindrical member 19 and a connecting portion 16 for the tube 89 at a rear end 11b of the cylindrical member 19. The tubes 89 are also cylindrical and provided with translucent side wall portions 89c. The liquid level detecting unit (photo interrupter) 110 includes a light emitting unit (light projecting unit) 111 and a light receiving unit 112 disposed opposite each other on both sides of the side wall portion 11c of the discharge head 11 at a first position P1 on an upstream side of the cavity 13 of the discharge head 11. This means that it is possible to detect the liquid level 25b of the liquid material 25 using the difference in the refractive index and the resulting difference in the direction of refraction of light due to the presence or absence of liquid material 25 inside the side wall portion 11c. In this embodiment, the liquid level 25b is detected at the first position P1 using the fact that light is transmitted from the light emitting unit 111 toward the light receiving unit 112 if the liquid material 25 is present inside the side wall portion 11c, while light from the light emitting unit 111 scatters if the liquid material 25 is not present inside the side wall portion 11c. The state estimating unit 81 includes a unit 81a that estimates the state of the liquid material 25 according to the liquid level 25b moving or reaching the predetermined position P1.

Figure 11:
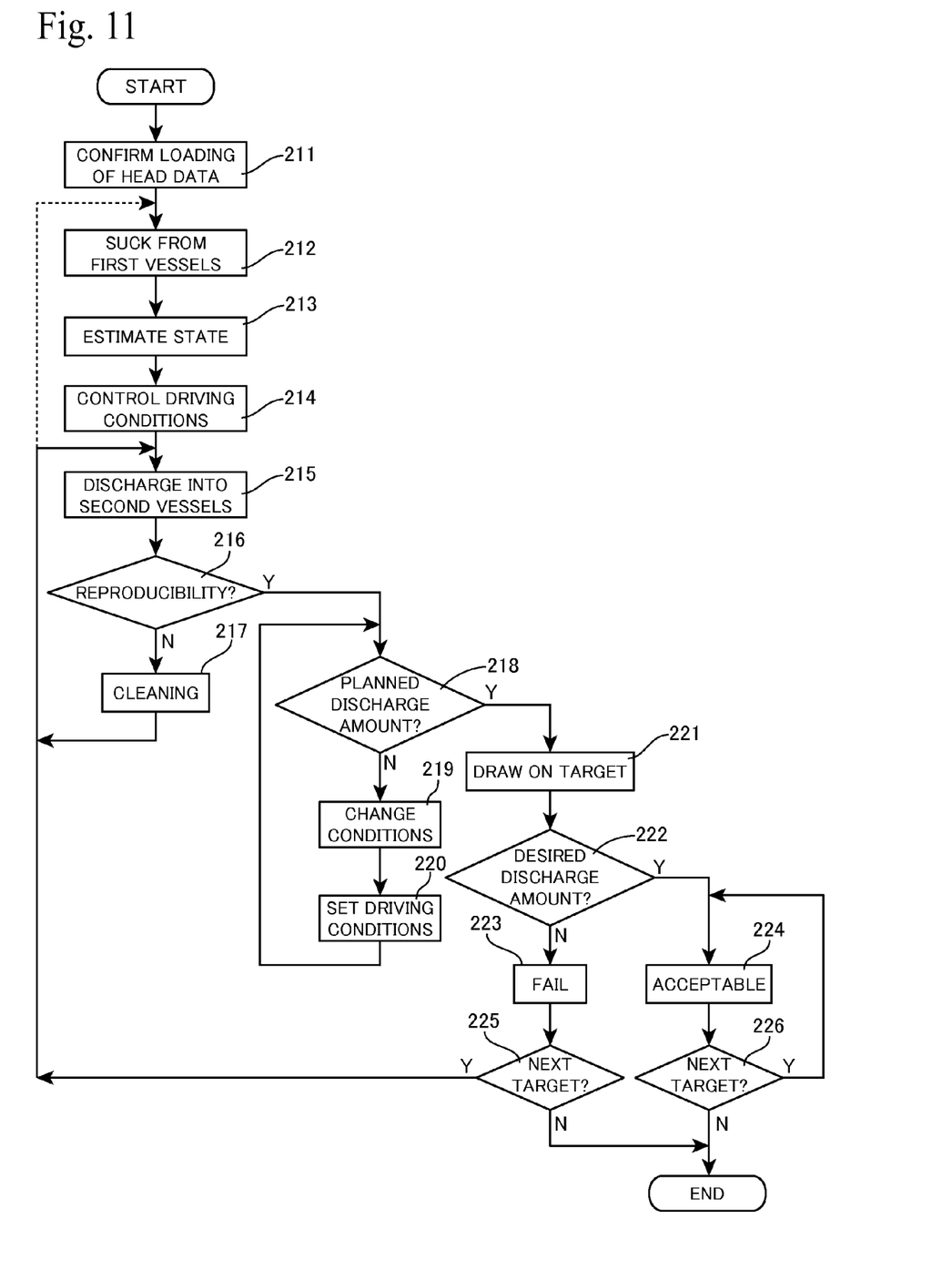
FIG. 11 is a flowchart of different processing by a control unit.

In this discharge system 1a, the first position P1 is set so that when the liquid level 25b of the liquid material 25 that has been sucked in from the nozzle opening 14 has reached the first position P1, the inside of the side wall portion 11c will have been filled with a predetermined suction amount a of the liquid material 25. This means that by starting the suction of liquid material 25 and measuring the suction time t until the liquid level detecting unit 110 detects the liquid level 25b using the suction time measuring unit 120, it is possible to measure the suction time t until the discharge head 11 has sucked in the predetermined suction amount a of the liquid material 25. Accordingly, in step 113, by substituting the suction time t of the liquid material 25 measured by the suction time measuring unit 120 into the approximation function f, it is possible to estimate the viscosity X of the liquid material 25. This means that it is possible to provide a discharge system 1a that is capable of setting a voltage or voltage pattern suited to discharging the liquid material 25 of the estimated viscosity X and carrying out stabilized discharge with a desired discharge amount, even with an unknown liquid material 25. Note that the position at which the liquid level detecting unit 110 is set may be the first position P1 that sandwiches the side wall portion 11c of the discharge head 11 or may be a second position P2 that sandwiches the side wall portion 89c of the tube 89. Also, by setting the first position P1 and the second position P2 downstream of (i.e., before) a liquid level position corresponding to a volume (suction amount) that can be sucked by the discharge head 11, it is possible to prevent sucking of the liquid material 25 beyond a suction limit. Also, the liquid level detecting unit 110 may be an image pickup unit (CCD camera) that picks up images of the liquid level 25b at the first position P1 or the second position P2 and may detect that the liquid level 25b has reached (passed) from images picked up by the CCD camera FIG. 11 shows an overview of different processing by the control unit 80 of the discharge systems 1 and 1a by way of a flowchart. In step 213, the state estimating unit 81 of the control unit 80 may estimate the state of the liquid material 25 sucked into the cavity 13, as examples, the viscosity, the surface tension, the number and form, diameter (size), shape, pattern, and color of particle materials included in the liquid material 25, or the specific gravity of the liquid. It is also possible to record information relating to the state of the liquid material 25 in the memory incorporated in the discharge head 11 in advance as the unique values (head data) of the discharge head 11 and to use such information when setting the driving conditions of the discharge head 11. In addition, in step 214, the estimated driving condition setting unit 82 of the control unit 80 may set conditions for driving the piezo elements 12 according to the estimated state of the liquid material 25, for example, by setting driving conditions that are capable of agitating the liquid material 25 by changing the internal pressure of the cavities 13 to a degree where the liquid material 25 is not discharged from the cavities 13, supplying driving pulses to the piezo elements 12 according to a pushing method or a pulling method, and changing the timing, pulse width, pulse height, and the like for supplying the driving pulses. Note that since the other steps are the same as the embodiment described above, description thereof is omitted.

Note that the target 51 onto which the liquid material 25 is discharged includes, as examples, known testing and experimental equipment such as microplates (well microplates), glass substrates, membranes, cell sources, films, silicon substrates, test tubes, and Petri dishes, and analytical equipment such as DNA microarrays (DNA chips) where a large number of DNA fragments are laid out with a high density on a substrate made of plastic or glass.

Although an example where a piezo element has been used as the actuator 12 has been described in the above embodiment, the actuator that varies (changes) the internal pressure of the cavity 13 may be a heater that produces bubbles inside the cavity using heat. Since a piezo element that is capable of changing the pressure inside a cavity using mechanical force is resistant to effects due to heat, a piezo element is favorable as an actuator. The discharge heads are not limited to heads where a flat plate-like piezoelectric element is attached to the outer surface of a cavity, and may be Gould-type head where a glass tube and a cylindrical piezoelectric element are combined.

Note that the present invention is not limited to the embodiments above and is defined by the range of the claims. Also, the inventions defined by the range of the claims may be independent from one another on a claim by claim basis.

The invention claimed is:

1. A discharge system comprising:
    a discharge head that discharges a liquid material onto a target from a nozzle opening that is communicated with a cavity by changing an internal pressure of the cavity using an actuator;
    a state estimating unit that estimates a state of the liquid material by sucking the liquid material from a first vessel holding the liquid material into the cavity via the nozzle opening;
    a driving condition setting unit that sets conditions for driving the actuator according to an estimated state of the liquid material;
    a weight measuring unit that measures a weight of a vessel group including the first vessel and of the liquid material held in the vessel group; and
    a first discharge amount confirming unit that measures, using the weight measuring unit, a change in weight when the discharge head has sucked from any vessel in the vessel group and a change in weight when the discharge head has discharged into any vessel in the vessel group and confirms a discharge amount of the discharge head;
    wherein the state estimating unit includes a viscosity estimating unit that estimates a viscosity of the liquid material according to a suction amount and a suction time when applying a predetermined pressure, and
    the driving condition setting unit includes a waveform control unit that controls a voltage applied to the actuator according to an estimated viscosity of the liquid material.

2. The discharge system according to claim 1, further comprising:
    a liquid level detecting unit that detects the liquid level of the liquid material when the discharge head has sucked the liquid material; and
    the state estimating unit includes a unit that estimates a state of the liquid material according to a liquid level moving or a liquid level reaching on a predetermined position.

3. The discharge system according to claim 2,
    wherein the liquid level detecting unit includes a sensor that detects the liquid level that has reached the predetermined position.

4. The discharge system according to claim 1,
    wherein the state estimating unit includes a unit that estimates the state of the liquid material according to a change in weight of the first vessel.

5. The discharge system according to claim 1, further comprising a second discharge amount confirming unit that measures, using the weight measuring unit, a change in weight when the discharge head has discharged into any vessel in the vessel group after discharging onto the target and confirms a discharge amount of the liquid material discharged onto the target.

6. The discharge system according to claim 1, further comprising:
    a weight measuring unit that measures a weight of a vessel group including the first vessel and of the liquid material held in the vessel group; and
    a second discharge amount confirming unit that measures, using the weight measuring unit, a change in weight when the discharge head has sucked from any vessel in the vessel group and a change in weight when the discharge head has discharged into any vessel in the vessel group after discharging onto the target, and confirms the discharge amount of a liquid material discharged onto the target.

7. The discharge system according to claim 1, further comprising:
    an image pickup unit that picks up an image of droplets discharged from the nozzle opening into any vessel in the vessel group; and
    a reproducibility checking unit that checks reproducibility of a discharge state of the droplets by comparing images recorded by the image pickup unit.

8. A discharge system comprising:
    a discharge head that discharges a liquid material onto a target from a nozzle opening that is communicated with a cavity by changing an internal pressure of the cavity using an actuator;
    a state estimating unit that estimates a state of the liquid material by sucking the liquid material from a first vessel holding the liquid material into the cavity via the nozzle opening;

a driving condition setting unit that sets conditions for driving the actuator according to an estimated state of the liquid material;

a weight measuring unit that measures a weight of a vessel group including the first vessel and of the liquid material held in the vessel group;

a first discharge amount confirming unit that measures, using the weight measuring unit, a change in weight when the discharge head has sucked from any vessel in the vessel group and a change in weight when the discharge head has discharged into any vessel in the vessel group and confirms a discharge amount of the discharge head;

an image pickup unit that picks up an image of droplets discharged from the nozzle opening into any vessel in the vessel group;

a reproducibility checking unit that checks reproducibility of a discharge state of the droplets by comparing images recorded by the image pickup unit; and a table moving unit that moves a table on which the target is placed, relative to the head unit so that the target is positioned below the discharge head, wherein the image pickup unit moves to a position that picks up images of the droplets in cooperation with movement of the table by the table moving unit.

9. The discharge system according to claim 8, further comprising a plurality of the discharge heads, wherein the state estimating unit includes a unit that estimates states of a plurality of liquid materials held in a plurality of vessels respectively by sucking the plurality of liquid materials using the plurality of discharge heads respectively, and the driving conditions setting unit includes a unit that sets conditions for driving respective actuators according to respective estimated states of the plurality of liquid materials.

10. A discharge system comprising:

a discharge head that discharges a liquid material onto a target from a nozzle opening that is communicated with a cavity by changing an internal pressure of the cavity using an actuator;

a state estimating unit that estimates a state of the liquid material by sucking the liquid material from a first vessel holding the liquid material into the cavity via the nozzle opening;

a driving condition setting unit that sets conditions for driving the actuator according to an estimated state of the liquid material;

a weight measuring unit that measures a weight of a vessel group including the first vessel and of the liquid material held in the vessel group; and a first discharge amount confirming unit that measures, using the weight measuring unit, a change in weight when the discharge head has sucked from any vessel in the vessel group and a change in weight when the discharge head has discharged into any vessel in the vessel group and confirms a discharge amount of the discharge head;

wherein the vessel group is mounted on the weight measuring unit, and the discharge system further comprises a conveying unit that moves the weight measuring unit relative to the discharge head.

11. The discharge system according to claim 10, further comprising a lock unit that restricts movement between the weight measuring unit and the discharge head.

12. The discharge system according to claim 11, wherein the lock unit includes:

a lock rod that moves up and down in cooperation with raising and lowering of the discharge head; and a lock plate operable to restrict, when the discharge head has been inserted in the first vessel, the movement of the lock rod in a horizontal direction and to fix a position of the discharge head.

13. The discharge system according to claim 10, further comprising a plurality of the discharge heads, wherein the state estimating unit includes a unit that estimates states of a plurality of liquid materials held in a plurality of vessels respectively by sucking the plurality of liquid materials using the plurality of discharge heads respectively, and the driving conditions setting unit includes a unit that sets conditions for driving respective actuators according to respective estimated states of the plurality of liquid materials.

14. The discharge system according to claim 1, further comprising a plurality of the discharge heads, wherein the state estimating unit includes a unit that estimates states of a plurality of liquid materials held in a plurality of vessels respectively by sucking the plurality of liquid materials using the plurality of discharge heads respectively, and the driving conditions setting unit includes a unit that sets conditions for driving respective actuators according to respective estimated states of the plurality of liquid materials.

\* \* \* \* \*